US010842965B2

(12) United States Patent
Haibach et al.

(10) Patent No.: US 10,842,965 B2
(45) Date of Patent: Nov. 24, 2020

(54) INTERCONNECT ASSEMBLY AND SUPPORT ASSEMBLY INCLUDING SAME

(71) Applicant: KONINKLIJKE PHILIPS N.V., Eindhoven (NL)

(72) Inventors: Richard Thomas Haibach, Verona, FL (US); Lauren Patricia Chodkowski, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 721 days.

(21) Appl. No.: 15/520,857

(22) PCT Filed: Oct. 15, 2015

(86) PCT No.: PCT/IB2015/057938
§ 371 (c)(1),
(2) Date: Apr. 21, 2017

(87) PCT Pub. No.: WO2016/067152
PCT Pub. Date: May 6, 2016

(65) Prior Publication Data
US 2017/0333660 A1 Nov. 23, 2017

Related U.S. Application Data

(60) Provisional application No. 62/072,569, filed on Oct. 30, 2014.

(51) Int. Cl.
*A61M 16/06* (2006.01)
*A62B 18/08* (2006.01)

(52) U.S. Cl.
CPC ..... *A61M 16/0683* (2013.01); *A44D 2203/00* (2013.01); *A61M 2209/088* (2013.01); *A62B 18/084* (2013.01)

(58) Field of Classification Search
CPC .............. A61M 16/0683; A61M 16/06; A44D 2203/00; A62B 18/084
(Continued)

(56) References Cited

U.S. PATENT DOCUMENTS 3,032,847 A 5/1962 Konrad
5,571,217 A 11/1996 Del Bon
(Continued)

FOREIGN PATENT DOCUMENTS

EP 0923887 A2 6/1999
JP 2012147980 A 8/2012
(Continued)

OTHER PUBLICATIONS

AirFit Nasal Mask N10, Resmed, Sep. 19, 2014.

*Primary Examiner* — Bradley H Philips
*Assistant Examiner* — Vincent D Hoang
(74) *Attorney, Agent, or Firm* — Michael W. Haas (57) ABSTRACT

An interconnect assembly (100, 300, 400) is for a support assembly (2) that includes a retention member (4) and a strap member (6). The interconnect assembly includes a number of female interconnect members (110, 210, 310, 410) with a first body member (112, 212, 312) and a first magnet (116, 216, 316, 416) coupled to the first body member. The first body member is connected to the retention member and has an aperture (114, 214, 314, 414). The interconnect assembly also includes a number of male interconnect members (150, 250, 350, 450) with a second body member (152, 252, 352) and a second magnet (160, 260, 360, 460) coupled to the second body member. The second body member is connected to the strap member and includes a protrusion (154, 254, 354, 452, 454) structured to be located within the aperture. When the protrusion is located within the aperture, the first magnet is attracted to the second magnet, thereby
(Continued)

removably connecting the first body member to the second body member.

14 Claims, 9 Drawing Sheets

(58) Field of Classification Search
USPC .................................................. 128/207.11
See application file for complete search history.

(56) References Cited

U.S. PATENT DOCUMENTS

| | | | |
|---|---|---|---|
| 5,630,258 A * | 5/1997 | Schneider | A44B 11/258 24/303 |
| 5,974,634 A * | 11/1999 | Eisenpresser | A44B 1/04 24/303 |
| 5,983,464 A | 11/1999 | Bauer | |
| 6,292,985 B1 * | 9/2001 | Grunberger | A44B 11/2592 24/303 |
| 6,598,271 B2 * | 7/2003 | Nire | A41F 1/002 24/265 WS |
| 7,341,060 B2 | 3/2008 | Nasr et al. | |
| 7,823,224 B2 | 11/2010 | Fullerton | |
| 8,042,542 B2 | 10/2011 | Nasr et al. | |
| 8,210,572 B2 | 7/2012 | Davis | |
| 10,143,270 B2 | 12/2018 | Fiedler et al. | |
| 2003/0196658 A1 * | 10/2003 | Ging | A61M 16/0057 128/201.22 |
| 2004/0112377 A1 * | 6/2004 | Amarasinghe | A61M 16/0633 128/201.22 |
| 2005/0155604 A1 | 7/2005 | Ging | |
| 2008/0314388 A1 * | 12/2008 | Brambilla | A61M 16/06 128/205.25 |
| 2010/0257898 A1 * | 10/2010 | Bonilla | A44C 5/2095 63/3.1 |
| 2014/0283826 A1 | 9/2014 | Jackson et al. | |

FOREIGN PATENT DOCUMENTS

| | | |
|---|---|---|
| PL | 67376 | 9/2014 |
| WO | 2006/074273 | 7/2006 |
| WO | WO2006096924 A1 | 9/2006 |
| WO | 2013/182952 | 12/2013 |
| WO | WO2014045245 A1 | 3/2014 |
| WO | 2014/110622 | 7/2014 |
| WO | 2014/110626 | 7/2014 |

\* cited by examiner

INTERCONNECT ASSEMBLY AND SUPPORT ASSEMBLY INCLUDING SAME

CROSS-REFERENCE TO RELATED APPLICATIONS

This patent application claims the priority benefit under 35 U.S.C. § 371 of international patent application no. PCT/IB2015/057938, filed Oct. 15, 2015, which claims the priority benefit under 35 U.S.C. § 119(e) of U.S. Provisional Application No. 62/072,569 filed on Oct. 30, 2014, the contents of which are herein incorporated by reference.

BACKGROUND OF THE INVENTION

1. Field of the Invention

The present invention relates generally to support assemblies, such as for example and without limitation, support assemblies for patient interface devices. The present invention further relates to interconnect assemblies for support assemblies.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. It is known to maintain such devices on the face of a wearer by a headgear having one or more straps adapted to fit over/around the patient's head. In order to connect the headgear to the mask frame, known patient interface devices employ clips. However, known clips are difficult to connect to the frame and to the headgear, and as such require undesirable expenditures of time to make these connections. Furthermore, when the patient desires to reverse the mask frame and have the opposite side of the mask frame face the patient, known clips require significant time to be disconnected and then reconnected to the opposing side.

There is thus room for improvement in interconnect assemblies and in support assemblies including interconnect assemblies.

SUMMARY OF THE INVENTION

In one embodiment, an interconnect assembly for a support assembly is provided. The support assembly includes a retention member and a strap member structured to be connected to the retention member. The interconnect assembly comprises a number of female interconnect members, at least one comprising a first body member and a first magnet coupled to the first body member, the first body member being connected to the retention member, the first body member having an aperture; and a number of male interconnect members, at least one comprising a second body member and a second magnet coupled to the second body member, the second body member being connected to the strap member, the second body member comprising a protrusion, the protrusion being structured to be disposed within the aperture. When the protrusion is disposed within the aperture, the first magnet is attracted to the second magnet, thereby removably connecting the first body member to the second body member.

In another embodiment, a support assembly comprises: a retention member; a strap member structured to be connected to the retention member; and an interconnect assembly comprising a number of female interconnect members, at least one comprising a first body member and a first magnet coupled to the first body member, the first body member being connected to the retention member, the first body member having an aperture, and a number of male interconnect members, at least one comprising a second body member and a second magnet coupled to the second body member, the second body member being connected to the strap member, the second body member comprising a protrusion, the protrusion being structured to be disposed within the aperture. When the protrusion is disposed within the aperture, the first magnet is attracted to the second magnet, thereby removably connecting the first body member to the second body member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "connected" or "coupled" together shall mean that the parts are joined or operate together either directly or through one or more intermediate parts or components. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
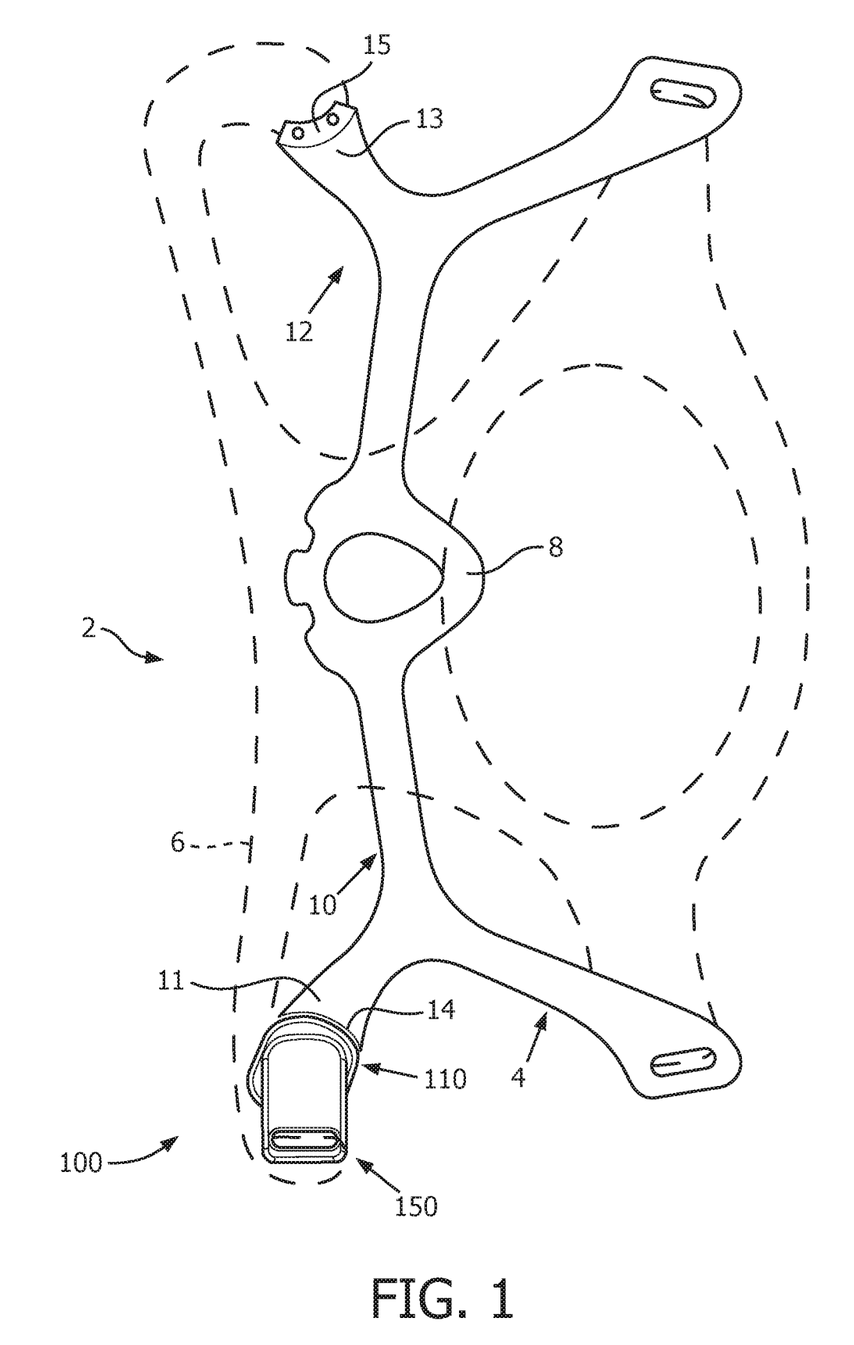
FIG. 1 is a simplified view of a portion of a support assembly according to one particular, non-limiting embodiment in which the present invention may be implemented.

FIG. 1 shows a support assembly 2 in accordance with a non-limiting embodiment of the disclosed concept. Support assembly 2 includes a retention member (e.g., without limitation, mask frame 4) and a strap member (e.g., without limitation, headgear strap 6, shown in simplified form in dashed line drawing) that is structured to be removably connected to mask frame 4. Support assembly 2 may be secured to the head of a patient, such as, for example and without limitation, during pressure support therapy in which a patient interface device (not shown) is employed. As will be discussed in greater detail below, support assembly 2 further includes an interconnect assembly 100 (partially shown in FIG. 1) that quickly and easily allows mask frame 4 to be removably connected to headgear strap 6.

Figure 6:
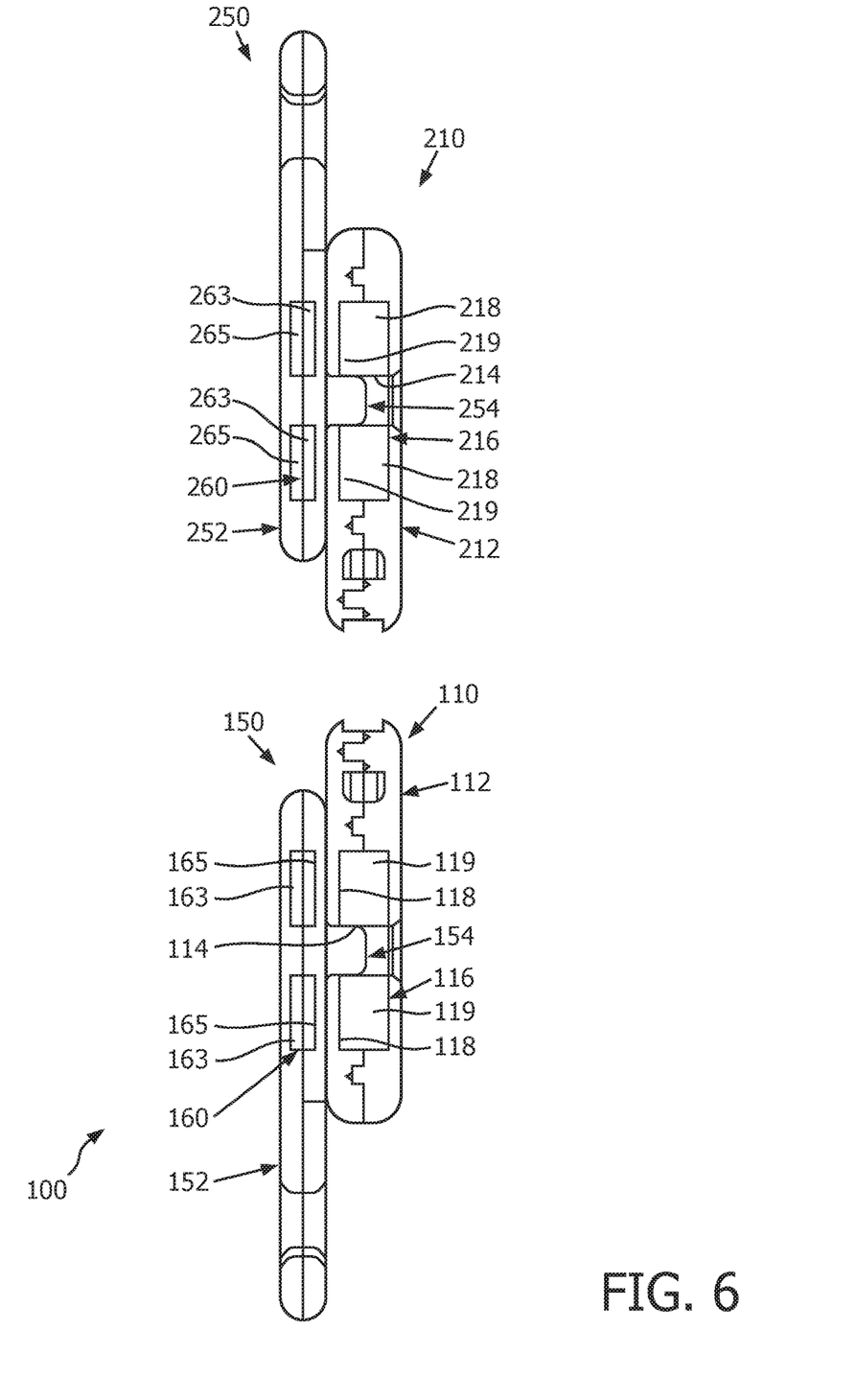
FIG. 6 is a simplified section view of the interconnect assembly of FIGS. 3A and 3B, shown with another female interconnect member and another male interconnect member.

Interconnect assembly 100 includes a number of female interconnect members (one female interconnect member 110 is shown and indicated in FIG. 1, see also female interconnect member 210 in FIG. 6) and a number of male interconnect members (one male interconnect member 150 is shown and indicated in FIG. 1, see also male interconnect member 250 in FIG. 6). For economy of disclosure, female interconnect member 110 and male interconnect member 150 will be described in detail herein, although it will be appreciated that female interconnect member 210 (FIG. 6) and male interconnect member 250 (FIG. 6) are employed with support assembly 2 in substantially the same manner, as will be discussed below.

Figure 2A:
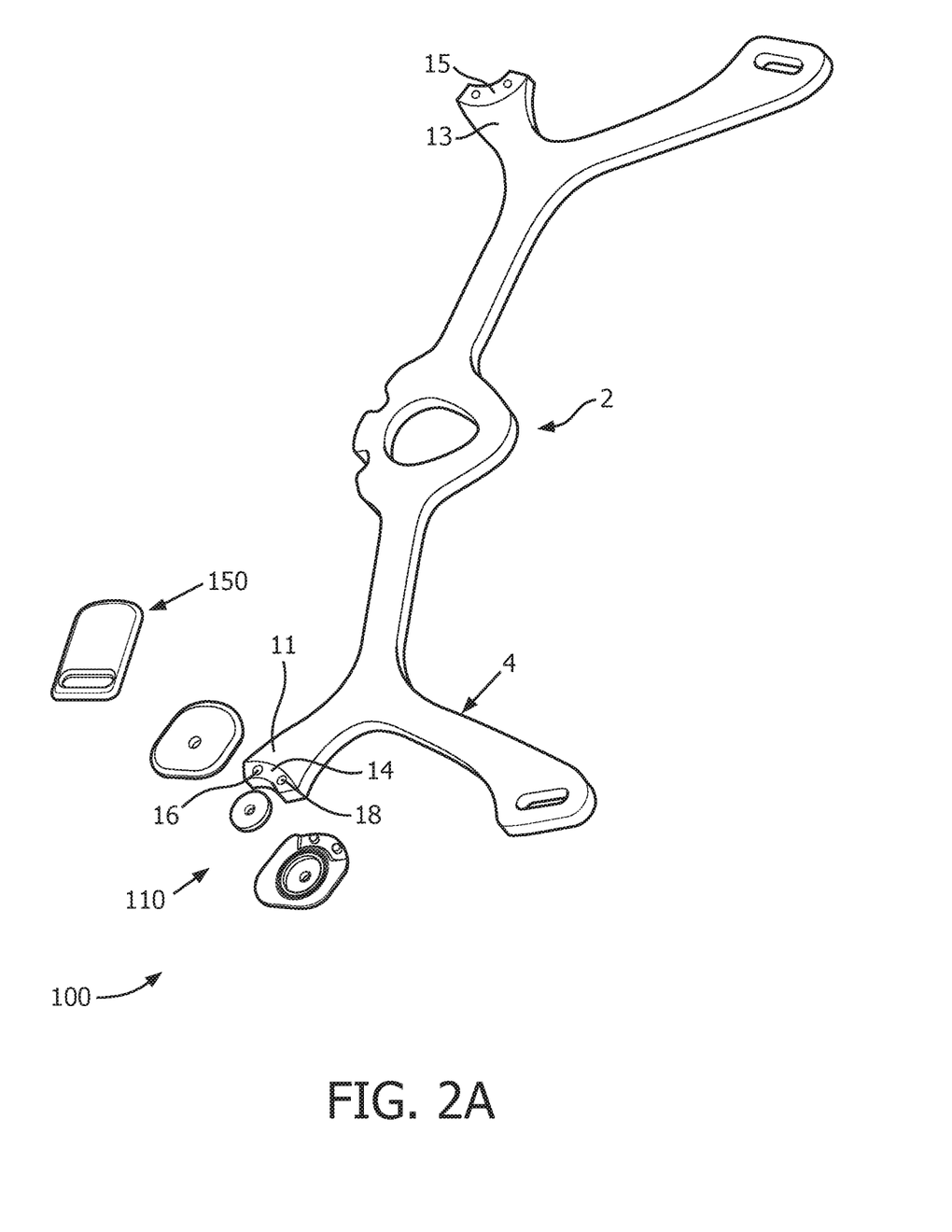
FIGS. 2A and 2B are exploded isometric views of the support assembly of FIG. 1, shown without the headgear strap.
Figure 2B:
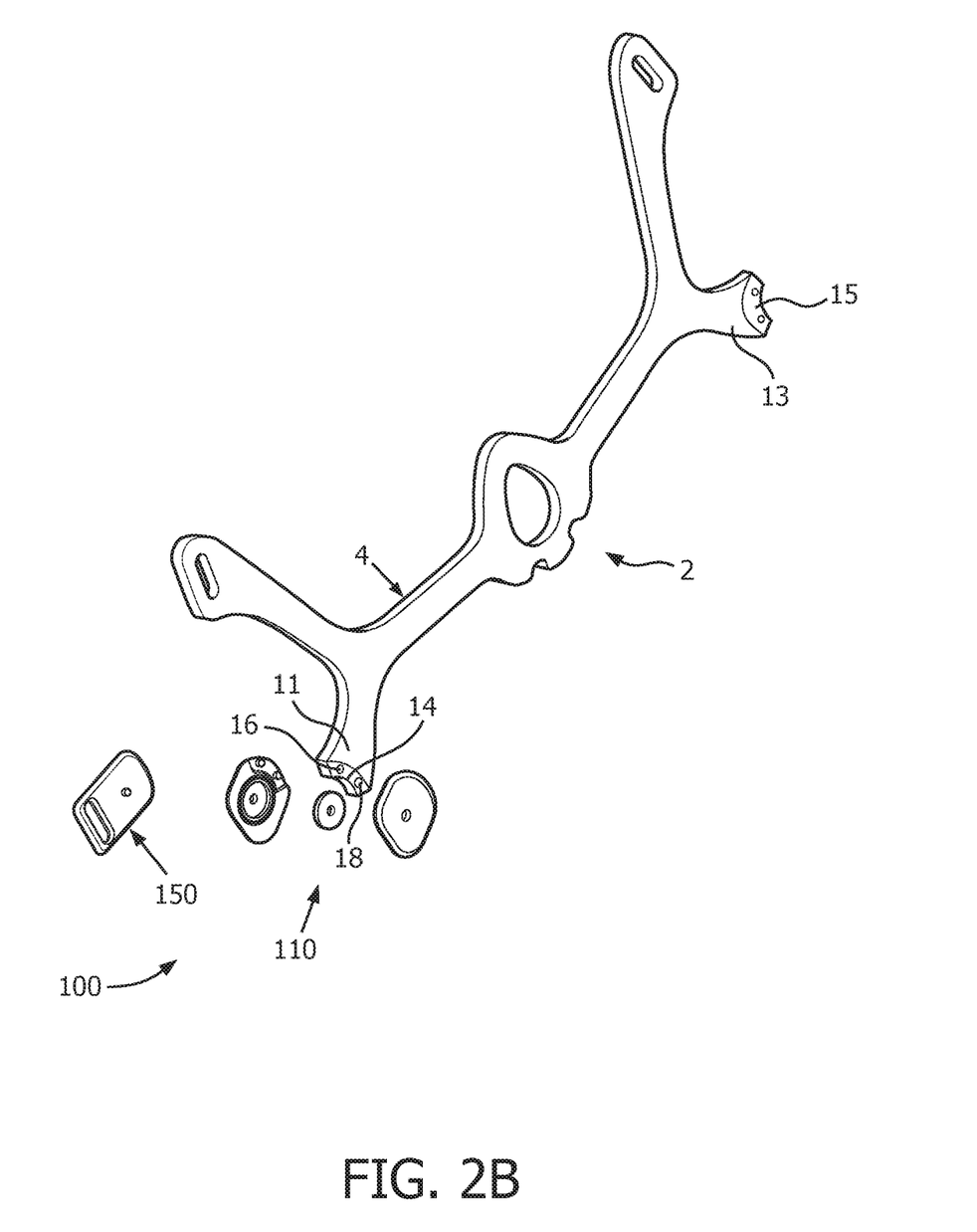

Mask frame 4 has a central location 8 that is located near a patient's nose, and a pair of Y-shaped arm portions 10,12 that extend from central location 8 in opposing directions. Arm portions 10,12 each have a pair of respective end portions (only end portions 11,13 are indicated). As shown in FIGS. 2A and 2B, end portion 11 has a number of thru holes (two thru holes 16,18 are shown and indicated). Female interconnect member 110 extends through thru holes 16,18 in order to advantageously connect headgear strap 6 (FIG. 1) to mask frame 4.

Figure 3A:
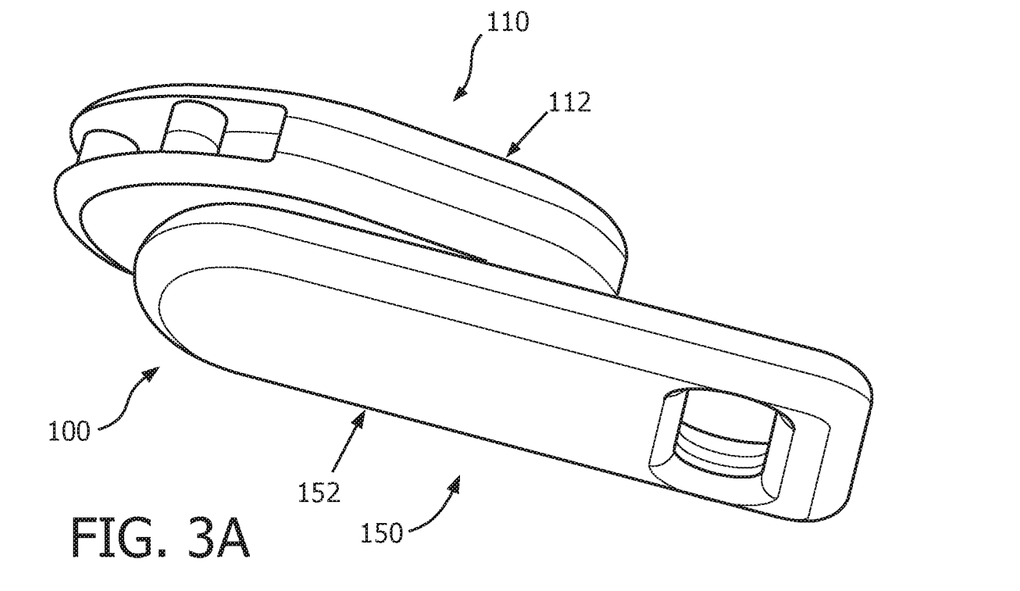
FIGS. 3A and 3B are isometric and exploded isometric views, respectively, of a portion of an interconnect assembly for the support assembly of FIG. 1.
Figure 3B:
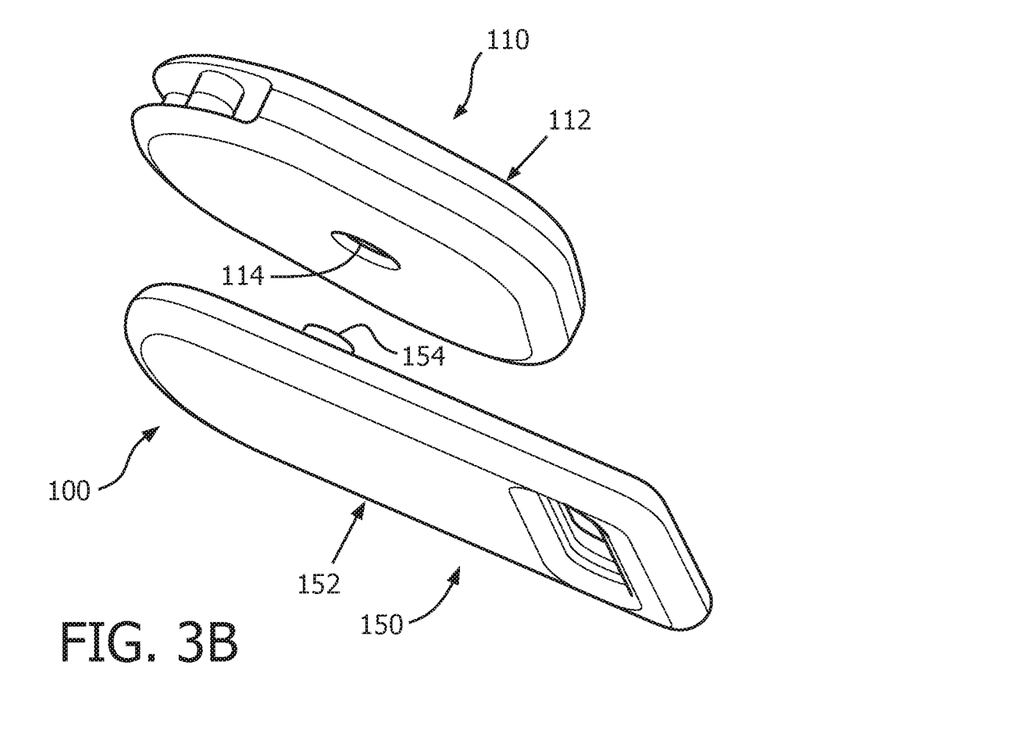

Referring to FIGS. 3A and 3B, female interconnect member 110 is removably connected to male interconnect member 150. More specifically, and with reference to FIG. 3B, female interconnect member 110 includes a body member 112 that has an aperture 114 and male interconnect member 150 includes a body member 152 that has a cylindrical-shaped protrusion 154. When protrusion 154 is located within aperture 114, female interconnect member 110 is magnetically attracted to male interconnect member 150, thereby removably connecting body member 112 to body member 152.

Figure 4A:
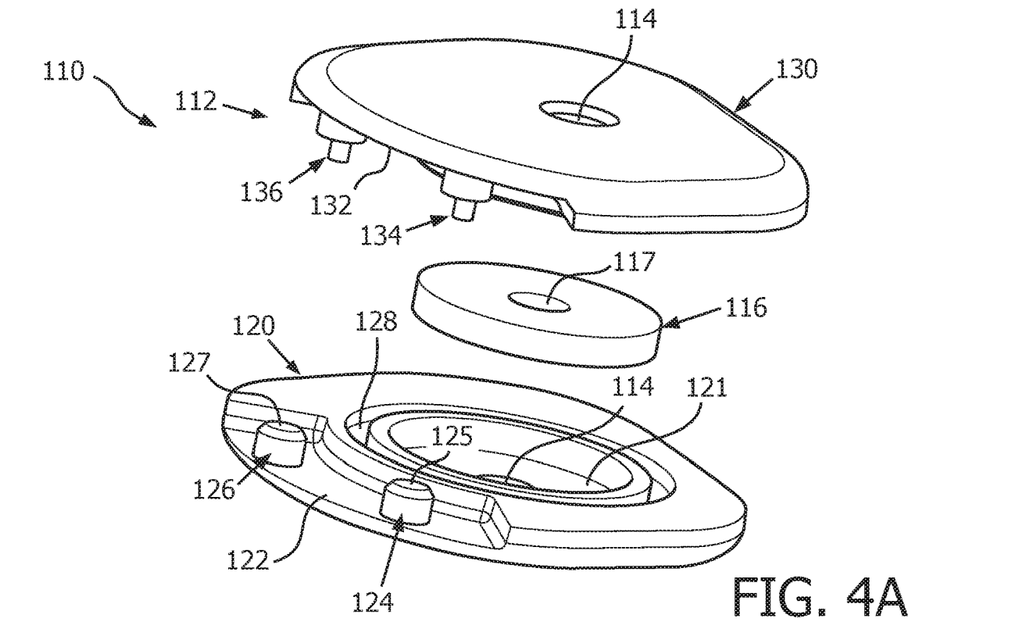
FIGS. 4A and 4B are exploded isometric views of a female interconnect member for the interconnect assembly of FIGS. 3A and 3B.
Figure 4B:
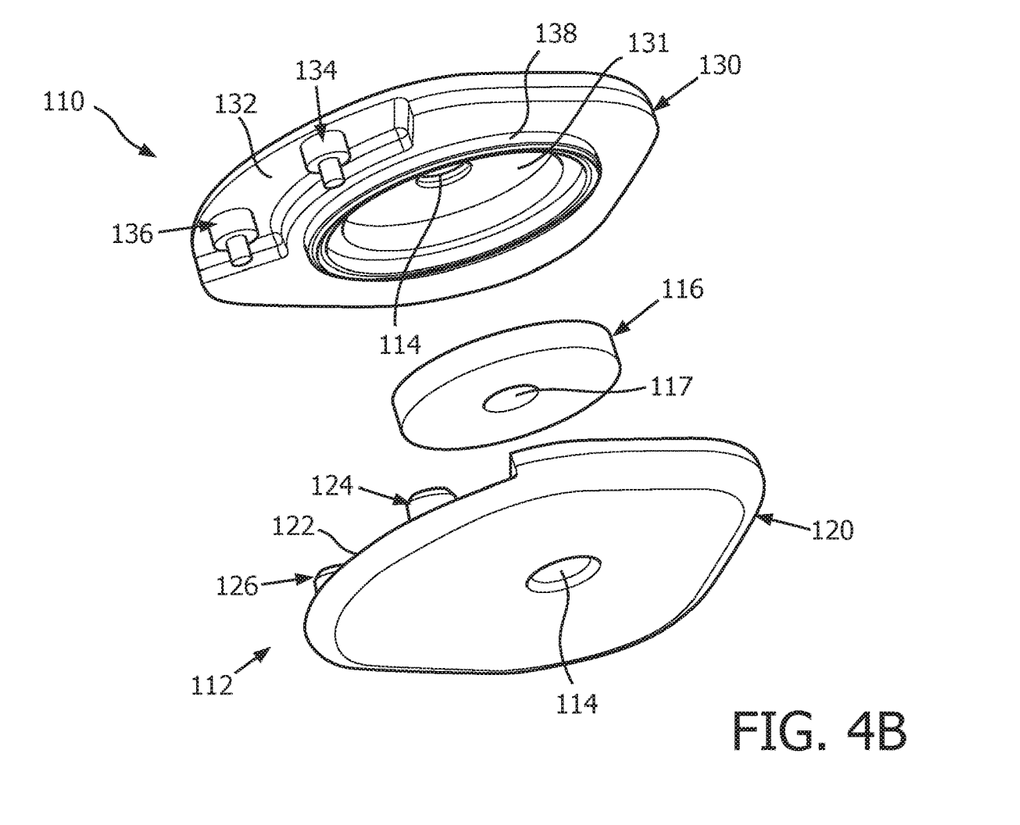

As shown in FIGS. 4A and 4B, body member 112 includes a number of containment portions 120,130. Containment portions 120,130 may be coupled by any suitable mechanism known in the art (e.g., without limitation, being ultrasonically welded or glued together). Containment portions 120,130 each have respective protruding lips 122,132 and respective posts 124,126,134,136. Posts 124,126 extend from protruding lip 122 toward protruding lip 132 and posts 134,136 extend from protruding lip 132 toward protruding lip 122. Additionally, posts 124,126 each have a respective opening 125,127. In operation, each of the posts 124,126, 134,136 extends through a corresponding one of thru holes 16,18 (FIGS. 2A and 2B), and posts 134,136 extend into openings 125,127 in order to advantageously connect body member 112 to mask frame 4. In this manner, protruding lips 122,132 are located on opposing sides of mask frame 4 to provide a relatively secure connection.

Additionally, containment portion 120 has an annular-shaped receiving portion 128 and containment portion 130 includes an annular-shaped flange 138 that extends into receiving portion 128 in order to further provide a secure connection between containment portions 120,130. As seen, containment portions 120,130 each have a respective pocket 121,131. Female interconnect member 110 further includes a disc-shaped magnet 116 that is coupled to body member 112 and has a thru hole 117 aligned with aperture 114. Magnet 116 is located within each of pockets 121,131 and is internal with respect to receiving portion 128 and flange 138.

Figure 5A:
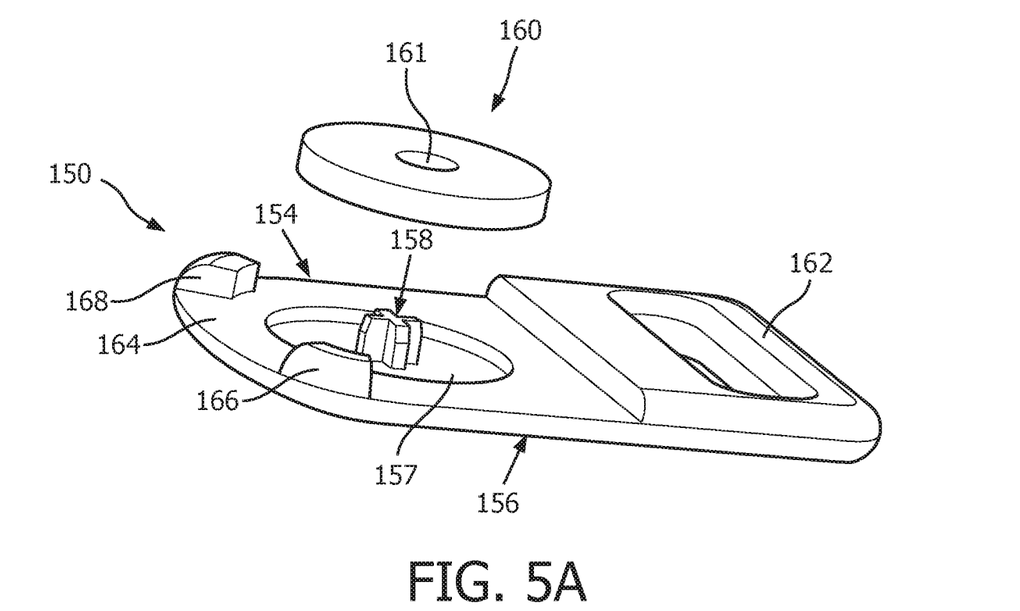
FIG. 5A is an exploded isometric view of a male interconnect member for the interconnect assembly of FIGS. 3A and 3B, shown with a portion of the male interconnect member removed to show hidden structures.
Figure 5B:
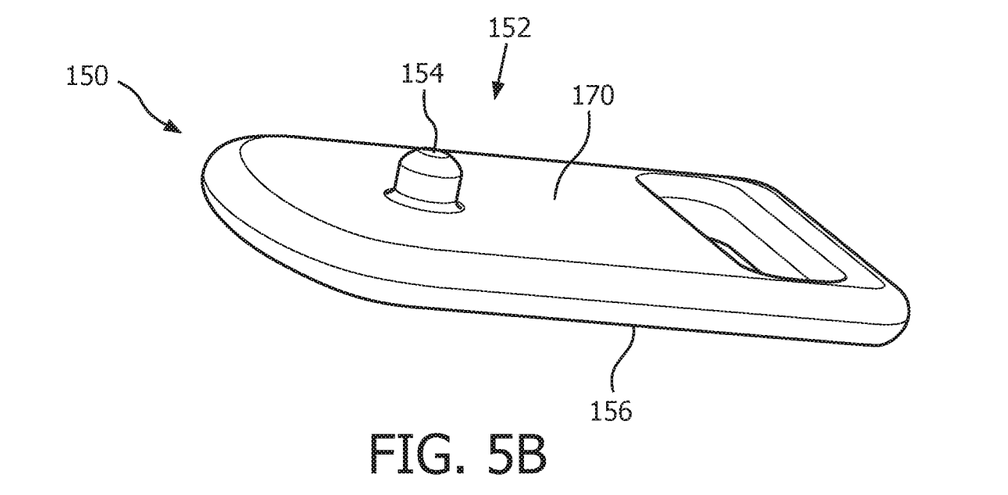
FIG. 5B is an isometric view of the male interconnect member of the interconnect assembly of FIGS. 3A and 3B.

FIG. 5A shows an exploded view of portions of male interconnect member 150, and FIG. 5B shows male interconnect member 150. Male interconnect member 150 is preferably made by an overmolding injection molding process. For example and without limitation, a first molded portion 156 is made by an injection molding process, a disc-shaped magnet 160 is placed on first molded portion 156, and then a second molded portion 170 is preferably molded over each of first molded portion 156 and magnet 160. It is however within the scope of the disclosed concept for a male interconnect member (not shown) to be made by any suitable alternative known method of embedding an object (i.e., magnet 160) within a body member (not shown) (e.g., without limitation, adhering two separate halves together with magnet 160 located between in a similar manner as female interconnect member 110).

Continuing to refer to FIG. 5A, magnet 160 has a thru hole 161, and protrusion 154 includes an X-shaped elongated body 158 that is located in first molded portion 156. Additionally, first molded portion 156 has a pocket 157. During assembly, magnet 160 is coupled to body member 152 by being placed into pocket 157, with elongated body 158 extending through thru hole 161. By employing X-shaped elongated body 158, magnet 160 is advantageously able to be well retained on first molded portion 156 when second molded portion 170 is molded over first molded portion 156 and magnet 160. However, it will be appreciated that a first molded portion (not shown) may have any suitable alternative shape and/or configuration in order to perform the desired function of retaining magnet 160 during the second stage of the molding process.

First molded portion 156 further has opposing end portions 162,164. End portion 162 is connected to headgear strap 6 (FIG. 1). Located near end portion 164 are a number of stabilizing projections (two stabilizing projections 166, 168 are shown and indicated). When second molded portion 170 is molded over first molded portion 156 and magnet 160, stabilizing projections 166,168 advantageously maintain first molded portion 156 within the associated mold (not shown).

FIG. 6 shows a section view of interconnect assembly 100. As seen, interconnect assembly 100 includes female interconnect member 110 and male interconnect member 150, and further includes opposing female interconnect member 210 and opposing male interconnect member 250 (wherein like reference numerals indicate like features). It will be appreciated that female interconnect member 210 and male interconnect member 250 are configured, and connected to support assembly 2 in substantially the same manner as female interconnect member 110 and male interconnect member 150. More precisely, female interconnect member 210 and male interconnect member 250 connect end portion 13 (FIG. 1) to headgear strap 6 (FIG. 1).

Referring again to FIGS. 1-2B, end portions 11,13 each include a respective recessed receiving portion 14,15. By having recessed receiving portions 14,15, interconnect assembly 100 advantageously exerts less pressure on a patient's face during use. Stated differently, when female interconnect members 110,210 are connected to respective recessed receiving portions 14,15, female interconnect members 110,210 protrude a smaller distance from respective end portions 11,13 towards the patient's face than if there were to be no recessed receiving portions 14,15. This results in a significantly more comfortable fit for the patient.

As shown in FIG. 6, magnet 116 substantially overlays and is magnetically attracted to magnet 160. More specifically, magnet 116 has a north pole 118 and a south pole 119. Magnet 160 has a north pole 163 and a south pole 165. As shown, north pole 118 is located between south pole 119 and magnet 160. Furthermore, north pole 118 and south pole 165 face each other and are magnetically attracted to each other. In other words, when protrusion 154 is located in aperture 114, magnets 116,160 are attracted to each other and advantageously enable body members 112,152 to be removably connected to each other. In this manner, when a patient desires to connect body members 112,152 to each other, and thus connect end portion 11 of mask frame 4 (FIG. 1) to headgear strap 6 (FIG. 1), the patient simply needs to insert protrusion 154 in aperture 114. In this configuration, magnets 116,160 will be properly positioned to be attracted to each other. Similarly, when a patient desires to disconnect body member 112 from body member 152, the patient need only apply a mechanical force greater than the magnetic force between magnets 116,160. As such, interconnect assembly 100 provides a significantly easier mechanism to connect mask frame 4 (FIG. 1) to and disconnect mask frame 4 (FIG. 1) from headgear strap 6 (FIG. 1).

Likewise, female interconnect member 210 includes a disc-shaped magnet 216 and male interconnect member 250 includes a disc-shaped magnet 260. Magnet 216 has a north pole 218 and a south pole 219, and magnet 260 has a north pole 263 and a south pole 265. As shown, south pole 219 is located between north pole 218 and magnet 260. Furthermore, south pole 219 and north pole 263 face each other and are magnetically attracted to each other. Additionally female interconnect member 210 has an aperture 214 and male interconnect member includes a protrusion 254 structured to be located in aperture 214. In a similar manner as female interconnect member 110 and male interconnect member 150, when protrusion 254 is located in aperture 214, magnets 216,260 are attracted to each other and advantageously enable respective body members 212,252 to be removably connected to each other, thus connecting end portion 13 (FIGS. 1-2B) to headgear strap 6 (FIG. 1). Thus, it will be appreciated that advantages associated with female interconnect member 110 and male interconnect member 150 likewise apply to female interconnect member 210 and male interconnect member 250.

Additionally, female interconnect members 110,210 and male interconnect members 150,250 advantageously have reversed polarities. Specifically, north pole 118 is located on the left side of female interconnect member 110 (e.g., with respect to south pole 119 in the orientation depicted in FIG. 6) and north pole 163 is located on the left side of male interconnect member 150 (e.g., with respect to south pole 165 in the orientation depicted in FIG. 6). By contrast, north pole 218 is located on the right side of female interconnect member 210 (e.g., with respect to south pole 219 in the orientation depicted in FIG. 6) and north pole 263 is located on the right side of male interconnect member 250 (e.g., with respect to south pole 265 in the orientation depicted in FIG. 6). In this manner, when a patient desires to reverse mask frame 4 (FIG. 1), male interconnect members 150,250 do not need to be disconnected from headgear strap 6 (FIG. 1). More precisely, because female interconnect members have reversed polarities, when mask frame 4 (FIG. 1) is reversed (not shown), female interconnect member 110 would overlay and be magnetically attracted to male interconnect member 250 and female interconnect member 210 would overlay and be magnetically attracted to male interconnect member 150. This advantageously results in less time to disconnect and reconnect mask frame 4 (FIG. 1) to headgear strap 6 (FIG. 1). By having reversed polarities, male interconnect members 150,250 need to only have one respective protrusion 154,254, as opposed to having a protrusion (not shown) on each side to accommodate a change in the polarity of a respective female interconnect member 110,210. In addition to the aesthetic improvement, this advantageously eliminates the possibility of an external protrusion (not shown) causing any discomfort to the patient.

Figure 7:
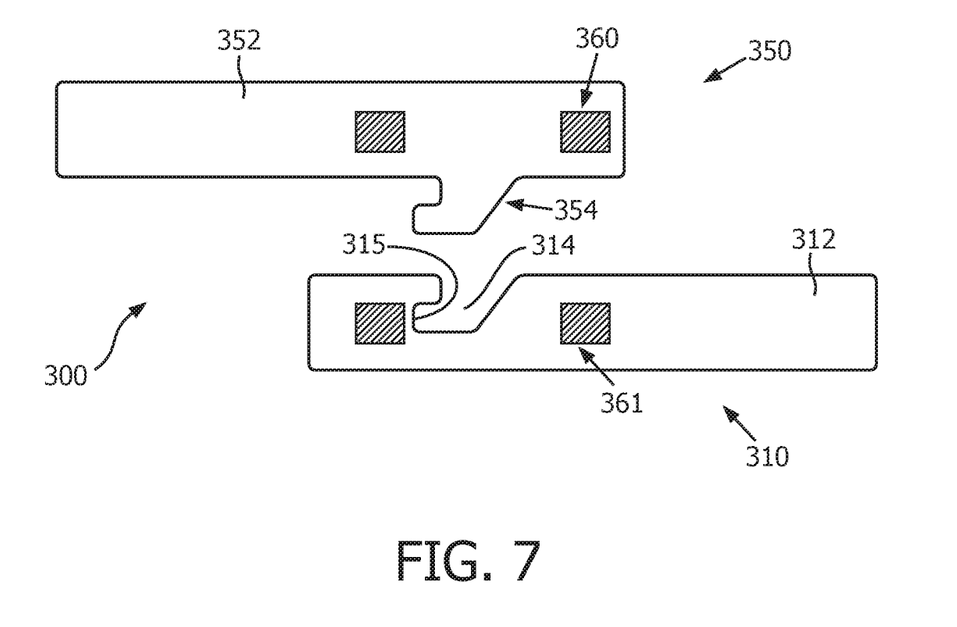
FIG. 7 is a simplified view of another interconnect assembly in accordance with an alternative non-limiting embodiment of the disclosed concept.

FIG. 7 shows a simplified view of an interconnect assembly 300 that may be implemented with support assembly 2 in place of interconnect assembly 100. As seen, interconnect assembly 300 includes a female interconnect member 310 and a male interconnect member 350. Each interconnect member 310,350 includes a respective body member 312, 352 coupled to a respective magnet 316,360. Furthermore, female interconnect member 310 has a receiving portion 315 that defines an aperture 314, and male interconnect member 350 includes a protrusion (e.g., without limitation, hook 354). When hook 354 is located in aperture 314, magnets 316,360 are attracted to each other, thereby removably connecting body member 312 to body member 352. Additionally, receiving portion 315 is shaped substantially similarly to hook 354. Thus, in addition to the magnetic force which connects body members 312,352 to each other, hook 354 provides an additional retention force to prevent body member 352 from becoming disconnected from body member 312 during use.

Figure 8:
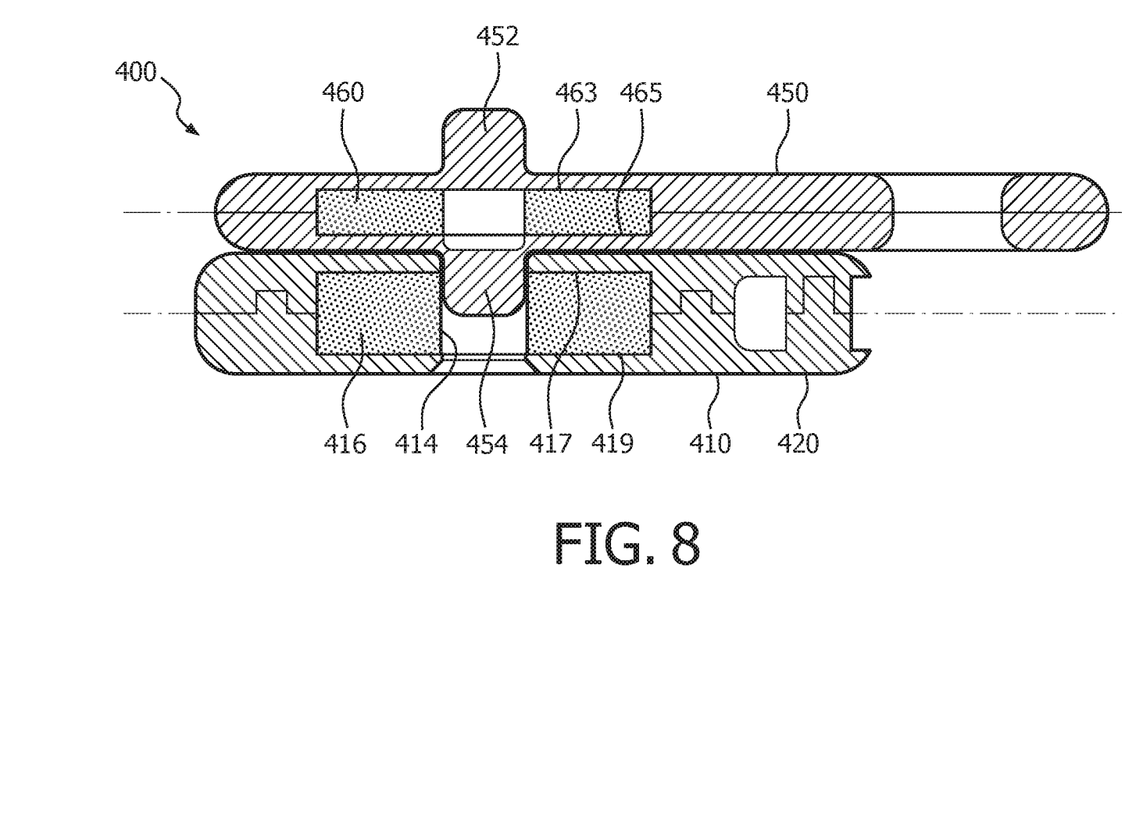
FIG. 8 is a simplified view of a still further interconnect assembly in accordance with an alternative non-limiting embodiment of the disclosed concept.

FIG. 8 shows a section view of interconnect assembly 400 that is generally similar to interconnect assembly 100 of FIG. 6. In this embodiment interconnect assembly 400 includes an female interconnect member 410 and male interconnect member 450. Male interconnect member 450 includes a magnet 460 having a north pole 463 and a south pole 465, a first post or protrusion 452 on one side thereof, and a second post or protrusion 454 on a second, opposite side thereof. Female interconnect member 410 includes a magnet 416 having a north pole 417 and a south pole 419, and an aperture 414 size and configured to receive either the first protrusion or the second protrusion.

This configuration for interconnect assembly 400 allows male interconnect member 450 to be flipped over from one side to another so that either first protrusion 452 or second protrusion 454 can engage aperture 414. In short, male interconnect member 450 is effectively reversible allowing either side to be exposed. Female interconnect member 410 includes a patient contacting surface 420, which can be formed in any manner suited for contacting a patient, such as flat, planar, smooth, padded, and/or contoured.

Accordingly, it will be appreciated that the disclosed concept provides an improved (e.g., without limitation, easier to assemble and disassemble) interconnect assembly 100,300 and support assembly 2 including the same, which among other benefits, employs magnets 116,160,216,260, 316,360 to quickly and easily allow mask frame 4 to be removably connected to headgear strap 6.

Additionally, although interconnect assemblies 100,300 have been disclosed in association with support assembly 2, it is within the scope of the disclosed concept for interconnect assemblies 100,300, or a similar suitable alternative interconnect assembly (not shown) to be employed with other assemblies (e.g., without limitation, book bags, purses, or other similar assemblies (not shown)).

While specific embodiments of the disclosed concept have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the disclosed concept which is to be given the full breadth of the claims appended and any and all equivalents thereof.

What is claimed is:

1. An interconnect assembly for a support assembly, the support assembly comprising a retention member and a strap member structured to be connected to the retention member, the interconnect assembly comprising:
    a number of female interconnect members, at least one comprising a first body member and a first magnet coupled to the first body member, the first body member being structured to be connected to the retention member, the first body member having an aperture; and
    a number of male interconnect members, at least one comprising a second body member and a second magnet coupled to the second body member, the second body member being structured to be connected to the strap member, the second body member comprising a generally cylindrical-shaped protrusion, the protrusion being structured to be disposed within the aperture, wherein, when the protrusion is disposed within the aperture, the first magnet is attracted to the second magnet, thereby removably connecting the first body member to the second body member,
    wherein the first body member comprises a first containment portion and a second containment portion,
    wherein the first containment portion is coupled to the second containment portion, wherein the first containment portion has a first pocket,
    wherein the second containment portion has a second pocket,
    wherein the first magnet is disposed within each of the first pocket and the second pocket,
    wherein the first containment portion comprises a number of first posts each having an opening, and
    wherein the second containment portion comprises a number of second posts each extending into a corresponding one of the openings.

2. The interconnect assembly of claim 1, wherein the first containment portion has an annular-shaped receiving portion, wherein the second containment portion comprises an annular-shaped flange extending into the annular-shaped receiving portion, and wherein the first magnet is disposed internal with respect to each of the annular-shaped receiving portion and the annular-shaped flange.

3. The interconnect assembly of claim 1, wherein the first containment portion comprises a first protruding lip, wherein the second containment portion comprises a second protruding lip, wherein the number of first posts is a plurality of first posts extending from the first protruding lip toward the second protruding lip, wherein the number of second posts is a plurality of second posts extending from the second protruding lip toward the first protruding lip, and wherein the first protruding lip and the second protruding lip are structured to be disposed on opposing sides of the retention member.

4. The interconnect assembly of claim 1, wherein the second body member has a first molded portion and a second molded portion molded over each of the first molded portion and the second magnet, wherein the first molded portion has a pocket, and wherein the second magnet is disposed within the pocket.

5. The interconnect assembly of claim 4, wherein the protrusion comprises an X-shaped elongated body, and wherein the X-shaped elongated body is disposed in the first molded portion.

6. The interconnect assembly of claim 4, wherein the first molded portion comprises a first end portion, a second end portion, and a number of stabilizing projections, wherein the first end portion is opposite the second end portion, wherein the first end portion is structured to be connected to the strap member, and wherein each of the stabilizing projections is disposed proximate the second end portion.

7. A support assembly comprising:
    a retention member;
    a strap member structured to be connected to the retention member; and
    an interconnect assembly comprising:
        a number of female interconnect members, at least one comprising a first body member and a first magnet coupled to the first body member, the first body member being connected to the retention member, the first body member having an aperture, and
        a number of male interconnect members, at least one comprising a second body member and a second magnet coupled to the second body member, the second body member being connected to the strap member, the second body member comprising a cylindrical-shaped protrusion, the protrusion being structured to be disposed within the aperture, wherein, responsive to the protrusion being disposed within the aperture, the first magnet is attracted to the second magnet, thereby removably connecting the first body member to the second body member,
    wherein the retention member is a mask frame for a patient interface device,
    wherein the strap member is a headgear strap for the patient interface device,
    wherein the mask frame comprises at least one end portion, wherein the at least one end portion has a number of thru holes, wherein the first body member comprises a first containment portion and a second containment portion, wherein the first containment portion has a number of first posts each having an opening, wherein the second containment portion comprises a number of second posts each disposed within a corresponding one of the openings of the first posts, and wherein each of the number of first posts and the number of second posts extends through a corresponding one of the thru holes of the at least one end portion in order to connect the mask frame to the first body member.

8. The support assembly of claim 7, wherein the at least one female interconnect member comprises a first female interconnect member and a second female interconnect member, wherein the at least one male interconnect member comprises a first male interconnect member and a second male interconnect member, wherein the retention member comprises a first end portion and a second end portion opposite the first end portion, wherein the first end portion comprises a first recessed receiving portion, wherein the second end portion comprises a second recessed receiving portion, wherein the first female interconnect member and the first male interconnect member connect the first recessed receiving portion to the headgear strap, and wherein the second female interconnect member and the second male interconnect member connect the second recessed receiving portion to the headgear strap.

9. The support assembly of claim 8, wherein the first magnet of the first female interconnect member has a first north pole and a first south pole, wherein the first north pole is disposed between the first south pole and the second magnet of the first male interconnect member, wherein the first magnet of the second female interconnect member has a second north pole and a second south pole, and wherein the second south pole is disposed between the second north pole and the second magnet of the second male interconnect member.

10. An interconnect assembly for a support assembly, the support assembly comprising a retention member and a strap member structured to be connected to the retention member, the interconnect assembly comprising:
 a number of female interconnect members, at least one comprising a first body member and a first magnet coupled to the first body member, the first body member being structured to be connected to the retention member, the first body member having an aperture; and
 a number of male interconnect members, at least one comprising a second body member and a second magnet coupled to the second body member, the second body member being structured to be connected to the strap member, the second body member comprising a protrusion, the protrusion being structured to be disposed within the aperture,
 wherein, when the protrusion is disposed within the aperture: the protrusion and the aperture are disposed between the first magnet and the second magnet and the first magnet is attracted to the second magnet, thereby removably connecting the first body member to the second body member,
 wherein the first body member comprises a first containment portion and a second containment portion,
 wherein the first containment portion is coupled to the second containment portion,
 wherein the first containment portion has a first pocket, wherein the second containment portion has a second pocket, and wherein the first magnet is disposed within each of the first pocket and the second pocket,
 wherein the first containment portion comprises a number of first posts each having an opening, and wherein the second containment portion comprises a number of second posts each extending into a corresponding one of the openings.

11. An interconnect assembly for a support assembly, the support assembly comprising a retention member and a strap member structured to be connected to the retention member, the interconnect assembly comprising:
 a number of female interconnect members, at least one comprising a first body member and a first magnet coupled to the first body member, the first body member being structured to be connected to the retention member, the first body member having an aperture; and
 a number of male interconnect members, at least one comprising a second body member and a second magnet coupled to the second body member, the second body member being structured to be connected to the strap member, the second body member comprising a protrusion, the protrusion being structured to be disposed within the aperture, wherein, when the protrusion is disposed within the aperture: the protrusion and the aperture are disposed between the first magnet and the second magnet and the first magnet is attracted to the second magnet, thereby removably connecting the first body member to the second body member,
 wherein the first magnet has a first thru hole aligned with the aperture of the first body member, wherein the second magnet has a second thru hole, and wherein the protrusion extends through the second thru hole, wherein each of the first magnet and the second magnet is disc-shaped, and wherein the first magnet substantially overlays the second magnet.

12. An interconnect assembly for a support assembly, the support assembly comprising a retention member and a strap member structured to be connected to the retention member, the interconnect assembly comprising:
 a number of female interconnect members, at least one comprising a first body member and a first magnet coupled to the first body member, the first body member being structured to be connected to the retention member, the first body member having an aperture; and
 a number of male interconnect members, at least one comprising a second body member and a second magnet coupled to the second body member, the second body member being structured to be connected to the strap member, the second body member comprising a protrusion, the protrusion being structured to be disposed within the aperture, wherein, when the protrusion is disposed within the aperture: the protrusion and the aperture are disposed between the first magnet and the second magnet and the first magnet is attracted to the second magnet, thereby removably connecting the first body member to the second body member,
 wherein the second body member has a first molded portion and a second molded portion molded over each of the first molded portion and the second magnet,
 wherein the first molded portion has a pocket, and wherein the second magnet is disposed within the pocket
 wherein the first molded portion comprises a first end portion, a second end portion, and a number of stabilizing projections,
 wherein the first end portion is opposite the second end portion, wherein the first end portion is structured to be connected to the strap member, and wherein each of the stabilizing projections is disposed proximate the second end portion.

13. The interconnect assembly of claim 11, wherein the protrusion comprises an X-shaped elongated body, and wherein the X-shaped elongated body is disposed in the first molded portion.

14. The interconnect assembly of claim 11, wherein the first molded portion comprises a first end portion, a second end portion, and a number of stabilizing projections, wherein the first end portion is opposite the second end portion, wherein the first end portion is structured to be connected to the strap member, and wherein each of the stabilizing projections is disposed proximate the second end portion.

\* \* \* \* \*